US012478722B2

(12) United States Patent
Couetil

(10) Patent No.: US 12,478,722 B2
(45) Date of Patent: Nov. 25, 2025

(54) BIDIRECTIONAL ARTERIAL CANNULA FOR EXTRACORPOREAL MEMBRANE OXYGENATION AND METHOD FOR USING SUCH A CANNULA

(71) Applicant: NOVAFLOW, Vaucresson (FR)

(72) Inventor: Jean-Paul Couetil, Vaucresson (FR)

(73) Assignee: NOVAFLOW, Vaucresson (FR)

( * ) Notice: Subject to any disclaimer, the term of this patent is extended or adjusted under 35 U.S.C. 154(b) by 852 days.

(21) Appl. No.: 17/776,683

(22) PCT Filed: Nov. 6, 2020

(86) PCT No.: PCT/FR2020/052022
§ 371 (c)(1),
(2) Date: May 13, 2022

(87) PCT Pub. No.: WO2021/099716
PCT Pub. Date: May 27, 2021

(65) Prior Publication Data

US 2022/0395621 A1 Dec. 15, 2022

(30) Foreign Application Priority Data

Nov. 18, 2019 (FR) ...................................... 1912831

(51) Int. Cl.
*A61M 1/32* (2006.01)
*A61M 1/36* (2006.01)
(Continued)

(52) U.S. Cl.
CPC ........ *A61M 1/3659* (2014.02); *A61M 25/003* (2013.01); *A61M 2025/0031* (2013.01); *A61M 25/0102* (2013.01)

(58) Field of Classification Search
CPC .............. A61M 1/3659; A61M 25/003; A61M 25/0043; A61M 25/0041; A61M 25/0074; A61M 2025/0031; A61M 2025/0078
See application file for complete search history.

(56) References Cited

U.S. PATENT DOCUMENTS 9,981,119 B2 * 5/2018 Walther ............ A61M 25/0043
2009/0275919 A1 * 11/2009 Todd ................. A61M 25/0102
604/509
(Continued)

FOREIGN PATENT DOCUMENTS

FR 3058642 A1 5/2018
RU 192289 U1 9/2019
(Continued)

OTHER PUBLICATIONS

International Search Report issued Mar. 22, 2021 re: Application No. PCT/FR2020/052022, pp. 1-2.

*Primary Examiner* — Laura A Bouchelle
(74) *Attorney, Agent, or Firm* — CANTOR COLBURN LLP

(57) ABSTRACT

An arterial cannula for ECMO includes a main arterial cannula with an inner wall and having a first end with a blood outflow port. The first end is intended to be introduced into an artery so as to inject the blood retrogradely into the artery. A retro-perfusion cannula is configured to be translatably movable between a retracted position in the first end of the main arterial cannula and a deployed position at least partly outside the main arterial cannula and opposite the blood outflow port of the main arterial cannula.

10 Claims, 6 Drawing Sheets

(51) Int. Cl.

| | |
|---|---|
| ***A61M 25/00*** | (2006.01) |
| *A61M 25/01* | (2006.01) |

(56) References Cited

U.S. PATENT DOCUMENTS

| | | | |
|---|---|---|---|
| 2012/0259273 | A1 | 10/2012 | Moshinsky et al. |
| 2016/0121079 | A1 | 5/2016 | Walther et al. |

FOREIGN PATENT DOCUMENTS

| | | | |
|---|---|---|---|
| SU | 406545 | A1 | 11/1973 |
| WO | 2016137212 | A1 | 9/2016 |

* cited by examiner

BIDIRECTIONAL ARTERIAL CANNULA FOR EXTRACORPOREAL MEMBRANE OXYGENATION AND METHOD FOR USING SUCH A CANNULA

TECHNICAL FIELD

The present disclosure concerns an arterial cannula for extracorporeal membrane oxygenation (ECMO) and a method for using such a cannula.

BACKGROUND

Extracorporeal membrane oxygenation (ECMO) refers to a method of emergency circulatory support for a patient with a cardiogenic shock. In the event of acute circulatory failure, this method is used at the patient's bedside in medical-surgical resuscitation irrespective of the reason for the heart failure. It is an extracorporeal circulation method, also used to perform open heart surgery. In the remainder of the description, reference will be made more specifically to oxygenation by extracorporeal venoarterial membrane (VA), allowing assisting both the heart and the lungs.

The goal of VA ECMO is to draw oxygen-poor blood out of the patient's body, load it with oxygen, and then pump it back into the patient's body. Blood is drawn at the right atrium (RA) of the patient's heart or from his inferior vena cava via a venous cannula, also called intake cannula. Afterwards, it passes through an oxygenator. Then it is reinjected in a retrograde manner, that is to say towards the heart, in the iliac artery or in the femoral artery of the patient via an arterial cannula, also called reinjection cannula. A centrifugal pump rotating at a constant speed, in the range of 3,000 rpm, enables this blood extracorporeal circulation. The rotational speed of the pump allows obtaining variable flow rates adapted to the needs of the patient.

The major drawback of this procedure is that a lower limb ischemia is observed due to the non-perfusion of the lower limb. Indeed, the arterial cannula obstructs the artery into which the blood is reinjected after oxygenation and therefore prevents the blood from circulating in the direction of the lower limb. It is then necessary to divert a portion of the blood oxygenated by the oxygenator, to send it in the femoral artery towards the lower limb, that is to say in the anterograde direction, downstream from the point of penetration of the arterial cannula with respect to the anterograde direction of blood flow. This derivation is generally achieved by a retroperfusion cannula or catheter as illustrated in FIG. 1. This involves delicate handling often carried out randomly often with difficulty, to introduce the retroperfusion cannula into the femoral artery.

FIG. 1 represents an arterial cannula 10 according to the prior art, including a main arterial cannula 12 and a retroperfusion cannula 14. The main arterial 12 and retroperfusion 14 cannulas comprise a first end, respectively 12' and 14', introduced into an artery 100 of a patient, such as for example the femoral artery, and are interconnected by their opposite end 10', to form the arterial cannula 10. The main arterial 12 and retroperfusion 14 cannulas are introduced into the artery 100 thanks to introducer stylets (not represented) which allow expanding the artery. Afterwards, the stylets are removed to enable blood to flow through the main arterial 12 and retroperfusion 14 cannulas. The retroperfusion cannula 14 is introduced into the artery 100 at a downstream penetration point "p", located downstream of an upstream penetration point P of the main arterial cannula 12, with respect to the direction of anterograde circulation of blood, from the heart to the lower limbs, represented by the arrow A. The arterial cannula 10 is connected to an oxygenator (not represented) to allow carrying out extracorporeal membrane oxygenation (ECMO). The oxygenator itself is in communication with a venous cannula (not represented) which allows drawing blood S at the right auricle or the inferior vena cava (not represented) of the patient's heart. During ECMO, the blood S circulates from the venous cannula (not represented), in the oxygenator (not represented), then in parallel in the main arterial cannula 12 and in the retroperfusion cannula 14. From the main arterial cannula 12, the blood is reinjected in a retrograde manner along the arrow F into the artery 100, that is to say according to the direction of retrograde circulation, in the direction of the iliac artery. From the retroperfusion cannula 14, the blood is reinjected into the artery 100, in the direction of antegrade circulation A, in the direction of the lower limbs. The main arterial cannula 12 being occlusive for the artery 100, the retroperfusion cannula 14 allows supplying the lower limb with blood.

In particular, the present disclosure aims at solving the aforementioned drawbacks.

SUMMARY

The disclosure provides an arterial cannula for ECMO comprising:

- a main arterial cannula including an inner wall and having a first end with a blood outlet orifice, the first end being intended to be inserted into an artery in order to inject blood in a retrograde manner into the artery, and
- a retroperfusion cannula configured to be movable in translation between a retracted position in the first end of the main arterial cannula and a position at least partially deployed out of the first end of the main arterial cannula, opposite to the blood outlet orifice of the main arterial cannula.

Thus, the arterial cannula according to the disclosure allows injecting blood into the artery in a retrograde manner, towards the heart, and in anterograde manner, towards the lower limb, in order to avoid the risk of ischemia and thrombosis generated by ECMO, while avoiding a delicate operation of introducing a retroperfusion cannula into a femoral artery.

According to other features of the disclosure, the cannula of the disclosure includes one or more of the following optional features considered separately or according to any possible combination.

According to one feature, the main arterial cannula has a L-like shape with a first branch corresponding to the first end intended to be introduced into the artery, and a second branch intended to cooperate with an oxygenator, the first branch and the second branch being connected by an elbow.

According to one feature, the elbow has an angle of curvature comprised between 90° and 150°, and preferably of 135°. In this way, the retroperfusion cannula is easily deployed out of the main arterial cannula.

According to one feature, the retroperfusion cannula comprises a tube with a diameter smaller than the diameter of the main arterial cannula and a ring with a diameter substantially identical to the diameter of the main arterial cannula, disposed at a proximal end of the retroperfusion cannula with respect to the blood outlet orifice of the main arterial cannula. Thus, the retroperfusion cannula is guided upon deployment thereof out of the main arterial cannula, and when the retroperfusion cannula is in the deployed position, it is retained in the main arterial cannula by its ring cooperating with the inner wall of the main arterial cannula, in order to prevent any misalignment or dislocation that might lead to hemolysis or arterial trauma.

According to one feature, the retroperfusion cannula is configured to slip in translation in contact with the inner wall of the main arterial cannula, until the ring comes into contact with a stop of the inner wall.

According to one feature, a cutout is present between the tube and the ring. This cutout is configured to cooperate with the elbow of the main arterial cannula. Furthermore, this cutout may be configured to cooperate with an introducer stylet configured to induce deployment of the retroperfusion cannula and to optimize the blood flow in the main arterial cannula when the retroperfusion cannula is in the deployed position.

According to one feature, the tube has a beveled distal end, opposite to the ring, so as to be adapted to the curvature of the elbow of the main arterial cannula when the retroperfusion cannula is in the retracted position. Thus, in the retracted position, the distal end of the tube is complementary to the elbow and does not project from the elbow, neither from inside nor from outside thereof, which allows for an easy slip of the arterial cannula out of the artery upon removal thereof.

According to one feature, the tube includes an opening directed towards the second branch of the main arterial cannula. The opening allows ensuring that blood could flow in the tube, even when the beveled distal end is obstructed. Indeed, the beveled distal end could be obstructed for example by the artery.

According to one feature, the beveled distal end has a wall including a first face with a length larger than an opposite second face, the first face comprising the opening directed towards the second branch of the main arterial cannula.

According to one feature, the tube has a beveled proximal end, proximate to the cutout, so as to be adapted to the curvature of the elbow of the main arterial cannula when the retroperfusion cannula is in the deployed position. Thus, in the deployed position, the proximal end of the tube is complementary to the elbow and does not project from inside the elbow, which allows for an easy circulation of blood in the main arterial cannula.

According to one feature, the tube has an elliptical profile, that is to say an elliptical cross-section. Thus, the height and bulk of the retroperfusion cannula in the retracted position inside the first end of the main arterial cannula or in the deployed position in the artery are minimized.

According to one feature, the tube of the retroperfusion cannula has a surface in the range of 3 to 3.5 mm2 and preferably of 3.15 mm2, with a height in the range of 1 to 1.5 mm and preferably 1.2 mm and a width in the range of 3 to 3.5 mm and preferably 3.34 mm. Thus, a minimum blood flow of 1 l/min is able to circulate in the tube. Such a flow is enough to prevent lower limb ischemia.

According to one feature, the ring has a convex inner wall. Thus, the switch from the deployed position into the retracted position of the retroperfusion cannula is facilitated. Furthermore, it allows laminating the blood flow and thus avoiding hemolysis and turbulent flows.

According to one feature, the main arterial cannula has a longitudinal groove at its inner wall cooperating with a rib disposed on the ring of the retroperfusion cannula. In this way, the translational mobility of the retroperfusion cannula in the main arterial cannula is guided. Furthermore, the groove forms a stop for the rib upon translation of the retroperfusion cannula, and this enables the ring to be disposed in contact with the inner wall of the main arterial cannula, in a regular manner, without a stop projecting into the main arterial cannula, and thus avoid turbulent flows and the risks of hemolysis.

According to one feature, the groove of the main arterial cannula has a length corresponding to the translation length of the retroperfusion cannula. Thus, the groove limits the translation of the retroperfusion cannula upon switching between the retracted and deployed positions.

Alternatively, the main arterial cannula has a translation portion of the ring, the translation portion having an inner diameter larger than the inner diameter of the rest of the main arterial cannula. Thus, the ring cooperates in translation with this translation portion and comes into abutment with the rest of the main arterial cannula, having a smaller diameter. Thus, the translation of the retroperfusion cannula is limited by an abutment effect of the ring conferred by the difference in the inner diameter of the main cannula, so that the distal end of the tube is flush with the elbow when the retroperfusion cannula is in the retracted position, and the proximal end of the tube is flush with the elbow in the deployed position.

According to one feature, the main arterial cannula has an aperture in its wall opposite to the blood outlet orifice, preferably with a diameter substantially identical to the diameter of the tube of the retroperfusion cannula, to enable the deployment of the tube in the artery. Thus, the retroperfusion cannula is easily deployed out of the main arterial cannula.

According to one feature, the aperture is disposed in the elbow of the main arterial cannula.

According to one feature, the inner wall of the main arterial cannula in contact with the retroperfusion cannula in the retracted position, is made of a rigid biocompatible material, such as a metallic material or polycarbonate. Thus, the retroperfusion cannula is adapted to slide easily in the main arterial cannula without the latter being able to be deformed during handling thereof. Furthermore, the main arterial cannula is not bulky so that it disturbs the blood flow to a minimum.

According to one feature, outside the inner wall in contact with the ring and the tube of the retroperfusion cannula, the main arterial cannula is made of a flexible material, such as nitinol or braided steel, preferably overmolded with a plastic material of the silicone or polyurethane type. Thus, the main arterial cannula is atraumatic and is easily introduced into the artery.

Furthermore, the flexible material is adapted to be deformed to allow conferring any shape on the main arterial cannula, in particular a Z-like shape with a first free branch corresponding to the first end intended to be introduced into the artery, a central branch and a second free branch intended to cooperate with an oxygenator. This Z-like shape allows reducing the spatial bulk of the set and fixing the cannula to the skin of a patient more easily while avoiding kinking of the cannula.

According to one feature, the retroperfusion cannula has a wall with a thickness in the range of 1 mm at most. Thus, the bulk is small.

According to one feature, the ring of the retroperfusion cannula is made of a rigid plastic, such as polyurethane, or of a biocompatible rigid metal such as steel. Thus, the translational guidance of the retroperfusion cannula is optimized.

According to one feature, the tube of the retroperfusion cannula is made of a composite material based on metal and plastic at its proximal end and of a flexible plastic such as silicone, at its distal end. Thus, the retroperfusion cannula is atraumatic at its distal end, and non-deformable at its proximal end.

According to one feature, the tube and the ring are connected by a metallic insert forming the cutout, such as a steel strip. Thus, the retroperfusion cannula has good mechanical strength.

According to one feature, the first end of the main arterial cannula includes at least one hole in its wall, proximate to its blood outlet orifice. Thus, the blood could be evacuated in the event of obstruction of the outlet orifice.

The disclosure further concerns an introducer stylet configured to be inserted into the arterial cannula as previously described, in order to enable both the insertion of the main arterial cannula into the artery and the deployment of the retroperfusion cannula out of the main arterial cannula, the introducer stylet being configured to obstruct the main arterial cannula. Thus, no blood flow circulates as long as the introducer stylet is disposed in the main arterial cannula.

According to one feature, the introducer stylet is configured to be obstructive in the first branch of the main arterial cannula and non-obstructive in the elbow and the second branch of this main arterial cannula. Thus, when the elbow is positioned in the artery, blood is able to enter the main arterial cannula via the aperture in its wall opposite to the blood outlet orifice, and blood is able to flow up into the second branch. An operator can then identify that the elbow is in the artery and therefore that the arterial cannula is in the proper position.

According to one feature, the introducer stylet has a shape complementary to the main arterial cannula with the retroperfusion cannula in the retracted position.

The introducer stylet is configured to be inserted into the main arterial cannula including the retroperfusion cannula in the retracted position, without coming into contact with the tube of the retroperfusion cannula, and configured to cooperate with the ring of the retroperfusion cannula to drive it in deployment upon removal thereof. Furthermore, the introducer stylet allows expanding the artery to facilitate the introduction of the main arterial cannula into the artery.

According to one feature, the introducer stylet includes a proximal end configured to be disposed in the first end of the main arterial cannula, the proximal end having a diameter increasing up to a diameter substantially identical to the diameter of the main arterial cannula, the proximal end being followed by a first intermediate portion with a length at least larger than that of the retroperfusion cannula and a diameter smaller than the diameter of the main arterial cannula, the first intermediate portion being followed by a second intermediate portion with a diameter substantially identical to that of the main arterial cannula.

According to one feature, the introducer stylet includes a recess complementary to the cutout of the retroperfusion cannula, and the recess includes a lug configured to drive the retroperfusion cannula in translation out of the arterial cannula when the introducer stylet is removed out the main arterial cannula.

According to one feature, the introducer stylet includes a groove in which the ring is intended to fit. Thus, the retroperfusion cannula is adapted to be held in the retracted position in the main arterial cannula upon insertion of the main arterial cannula into an artery, and adapted to be driven into its deployed position upon removal of the introducer stylet out of the arterial cannula.

According to one feature, the groove is complementary to the convex inner wall of the ring, so as to form an elastic semi-retentive system when the convex inner wall of the ring fits in the groove of the introducer stylet. Thus, the retroperfusion cannula is adapted to be held in the retracted position in the main arterial cannula upon insertion of the main arterial cannula into an artery, and adapted to be driven into its deployed position upon removal of the introducer stylet of the arterial cannula. When the ring comes into abutment upon deployment of the retroperfusion cannula, the introducer stylet continues its translation alone by a pulling effect exerted thereon by an operator.

According to one feature, the introducer stylet is perforated axially at its center in a hollow cylinder enabling the passage of a guide.

The disclosure also concerns a removal stylet configured to be inserted into the arterial cannula as previously described, in order to allow retracting the retroperfusion in the main arterial cannula, and to allow removing the main arterial cannula out of the artery, the removal stylet being configured to obstruct the main arterial cannula.

According to one feature, the removal stylet is perforated axially at its center in a hollow cylinder enabling the passage of a guide.

According to one feature, the removal stylet comprises a bulge configured to cooperate with the ring of the retroperfusion cannula in order to drive it in translation into the main arterial cannula, when the removal stylet is inserted into the main arterial cannula.

The disclosure also concerns a kit comprising an arterial cannula, an introducer stylet and a removal mandrel, as previously described.

DETAILED DESCRIPTION OF THE DRAWINGS

Figure 1:
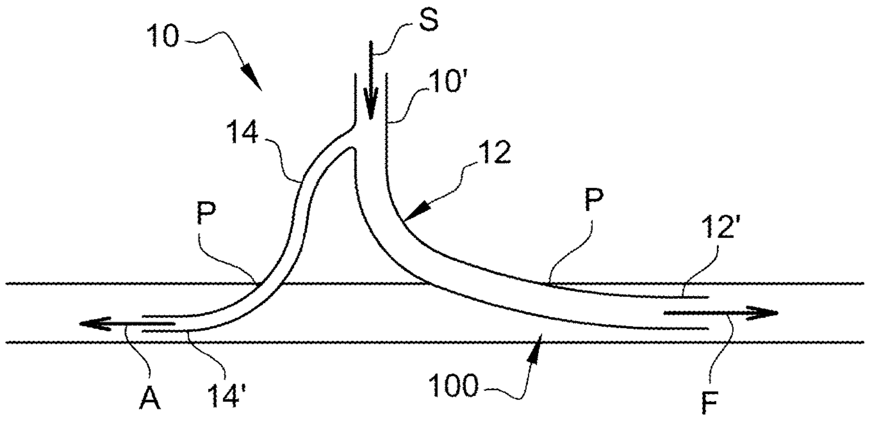
FIG. 1 is a schematic view of a main arterial cannula and a retroperfusion cannula according to the prior art.

FIG. 1 has been described before.

Figure 2:
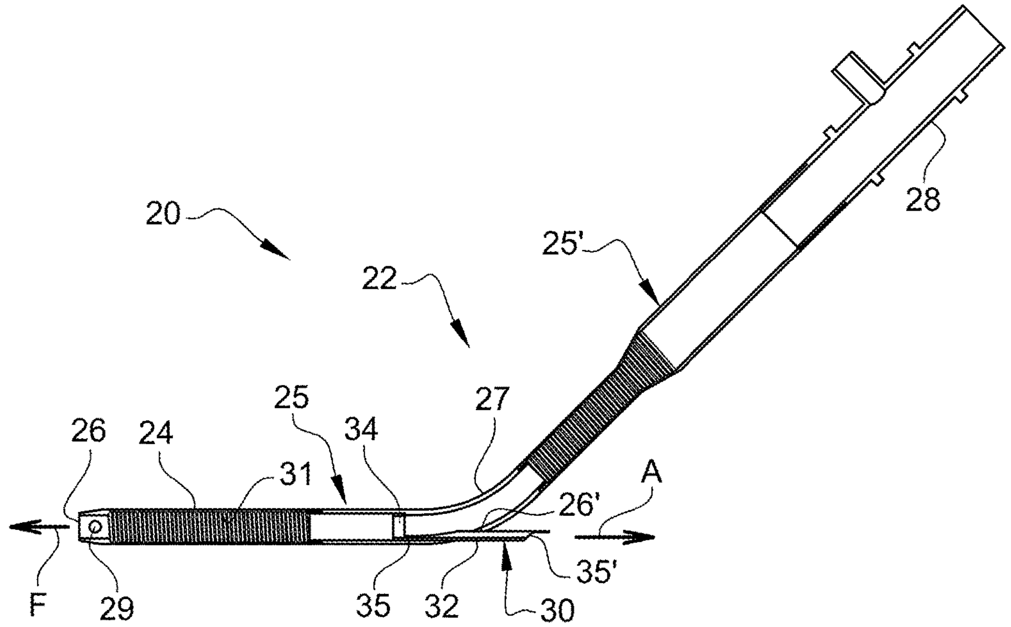
FIG. 2 represents an arterial cannula for ECMO according to the present disclosure, in longitudinal section.

FIG. 2 illustrates an arterial cannula 20 according to the present disclosure.

The arterial cannula 20 has a main arterial cannula 22 having a first end 24 comprising a blood outlet orifice 26, and a second end 28 intended to be connected to an oxygenator (not represented).

The main arterial cannula 22 may have an L-like shape, a first branch of which 25 comprises the first end 24, and a second branch 25' comprises the second end 28. The first 25 and second 25' branches may be connected by an elbow 27 which could have an angle of curvature of 135° on average and which could vary from 90° to 150°.

The first end 24 is configured to be introduced into an artery (not represented) in order to inject the blood in a retrograde manner according to the arrow F, into the artery. It includes a retroperfusion cannula 30 configured to be movable in translation between a retracted position (FIG. 6) in the first end 24 of the main arterial cannula 22 and a deployed position (FIG. 2) in the artery, partially out of the main arterial cannula 22, opposite to the blood outlet orifice 26 of the main arterial cannula 22. The retroperfusion cannula 30 is intended to inject blood into the artery in an anterograde manner, according to the arrow A.

The first end 24 of the main arterial cannula 22, as well as the retroperfusion cannula 30, may be rectilinear.

The main arterial cannula 22 may include, at its end proximal to the blood outlet orifice 26, a hole 29 allowing the blood to be evacuated in the event of an obstruction of the outlet orifice 26.

The main arterial cannula 22 may be formed primarily of nitinol or braided steel overmolded with silicone or polyurethane. It may have a portion in contact with the retroperfusion cannula 30 in the retracted position, made of polycarbonate. Thus, it may have a flexible portion made of nitinol or steel, and a rigid portion made of polycarbonate.

The retroperfusion cannula comprises a proximal end 35 with respect to the blood outlet orifice 26 of the main arterial cannula, and an opposite distal end 35'.

As illustrated in more detail in FIGS. 3 to 6, the retroperfusion cannula 30 may comprise a tube 32 such as an elliptical tube, having for example a surface of 3.15 mm2, a height "h" of 1 2 mm, a width L of 3.34 mm and a length "I" in the range of 5 to 15 mm. The retroperfusion cannula 30 may also comprise a ring 34 such as a circular ring. The ring 34 can be metallic or made of polyurethane. It may have a diameter D very slightly smaller than the inner diameter D' of the main arterial cannula allowing the retroperfusion cannula to slip without difficulty in the main arterial cannula. The tube 32 may comprise a proximal end 36 with respect to the blood outlet orifice 26 of the main arterial cannula 22, and an opposite so-called distal end 36'. The ring 34 may be disposed at the proximal end 35 of the retroperfusion cannula 30. It may be separated from the tube 32 by a cutout 38. The proximal 36 and distal 36' ends of the tube 32 may be oblique, that is to say beveled.

The beveled distal end 36' may be adapted to the curvature of the elbow 27 of the main arterial cannula when the retroperfusion cannula 30 is in the retracted position. Thus, in the retracted position, the distal end 36' of the tube 32 is complementary to the elbow 27. It does not project from the elbow 27, neither from inside nor from outside thereof, which allows for an easy slip of the arterial cannula out of the artery upon removal thereof. The beveled distal end 36' forms a blood passage orifice configured to direct blood opposite to the second branch 25' of the main arterial cannula 22.

Figure 17:
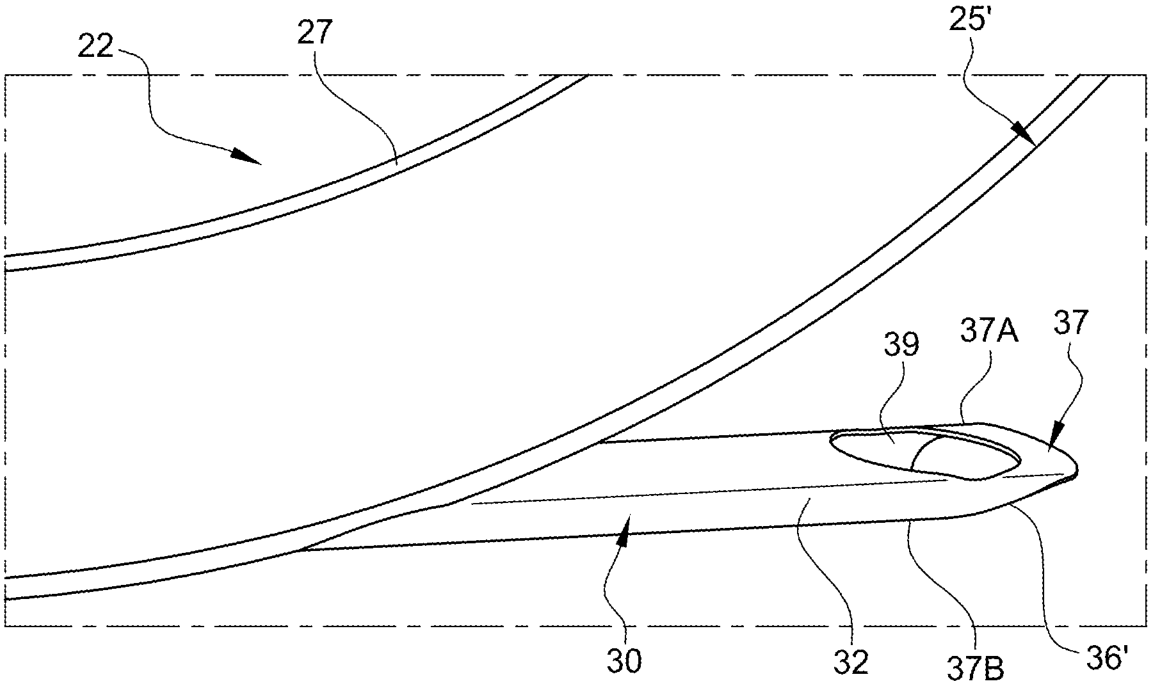
FIG. 17 is a schematic perspective view of a portion of the arterial cannula of FIG. 2, including a retroperfusion cannula according to one variant.
Figure 18:
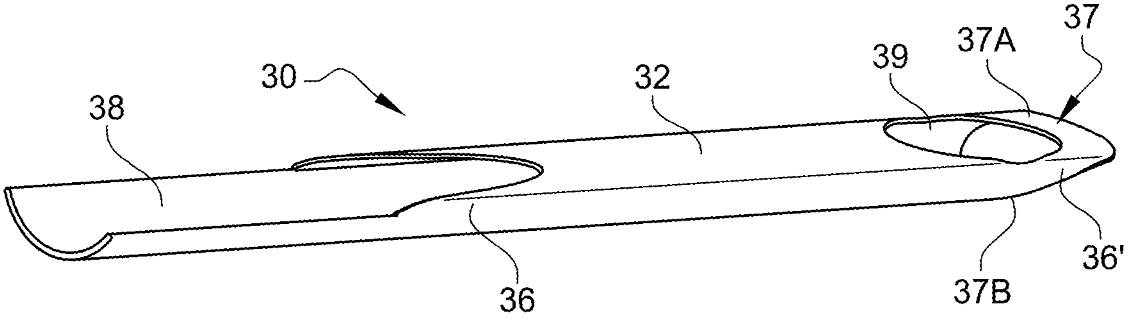
FIG. 18 is a schematic perspective view of a portion of the retroperfusion cannula illustrated in FIG. 17.

As shown in FIGS. 17 and 18, the tube 32 may include an opening 39 directed towards the second branch 25' of the main arterial cannula 22. The opening may be disposed at the distal end 36' of the tube 32.

The beveled distal end 36' may have a wall 37 including a first face 37A with a length larger than an opposite second face 37B, the first face 37A comprising the opening 39 directed towards the second branch 25' of the main arterial cannula 22. The opening allows ensuring that blood could flow through the tube, even when the beveled distal end is obstructed. Indeed, the beveled distal end could be obstructed for example by the artery.

The beveled proximal end 36 of the tube 32 may be arranged proximate to the cutout 38. It may be adapted to the curvature of the elbow 27 of the main arterial cannula 22 when the retroperfusion cannula 30 is in the deployed position. Thus, in the deployed position, the proximal end 36 of the tube is complementary to the elbow and does not project from inside the elbow, which allows for an easy circulation of blood in the main arterial cannula.

The main arterial cannula 22 may have a translation portion T (FIG. 11) of the ring 34 with a length identical to the length "I" of the tube 32. The translation portion T may be arranged at the first end 24 of the main arterial cannula 22.

The ratio between the inner diameter D' of the main arterial cannula and the inner diameter of the tube 32 of the retroperfusion cannula 30 may be 8.

The retroperfusion cannula 30 may have a wall having a thickness "e" of 0.1 mm.

An aperture 26' (FIG. 3), such as an elliptical lumen, may be present in the elbow 27 of the main arterial cannula 22, opposite to the blood outlet orifice 26, to enable the retroperfusion cannula 30 to be deployed out of the main arterial cannula 22. The aperture 26' may have a shape and dimensions identical to the shape and dimensions of the cross-section of the tube 32. Thus, only tube 32 is able to be deployed in the artery through the aperture 26'.

Figure 3:
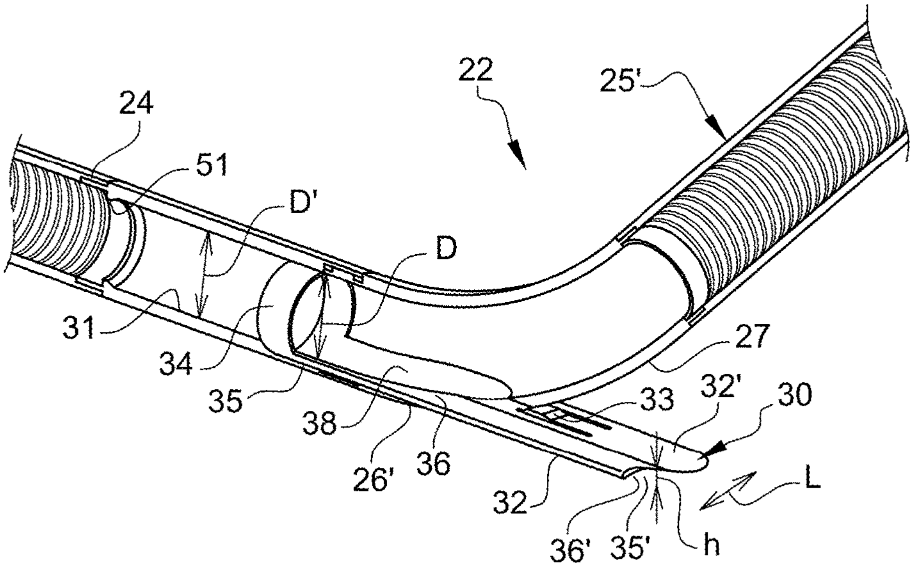
FIG. 3 is a schematic view in longitudinal section of a portion of the arterial cannula of FIG. 2.

FIG. 3 further shows that the first end 24 of the main arterial cannula 22 may have an inner wall 31 in contact with which the tube 32 and the ring 34 of the retroperfusion cannula are configured to slip. Thus, the tube 32 could be disposed in contact with the inner wall 31.

Furthermore, the tube 32 of the retroperfusion cannula 30 may have a bulge 33, for example flexible, configured to block the retroperfusion cannula 30 in the deployed position. The bulge 33 may be disposed on an upper portion 32' of the tube 32. The bulge 33 may be directed towards the second end 28 of the main arterial cannula 22. It could cooperate with the aperture 26' of the elbow 27. More specifically, it could cooperate with an outer and upper portion of the aperture 26' of the elbow 27 of the main arterial cannula 22. The bulge 33 allows preventing a spontaneous removal of the retroperfusion cannula 30 in the main arterial cannula.

The tube 32 may be made of a biocompatible composite material. It may include a portion at the cutout 38 in the form of a steel strip.

Figure 4:
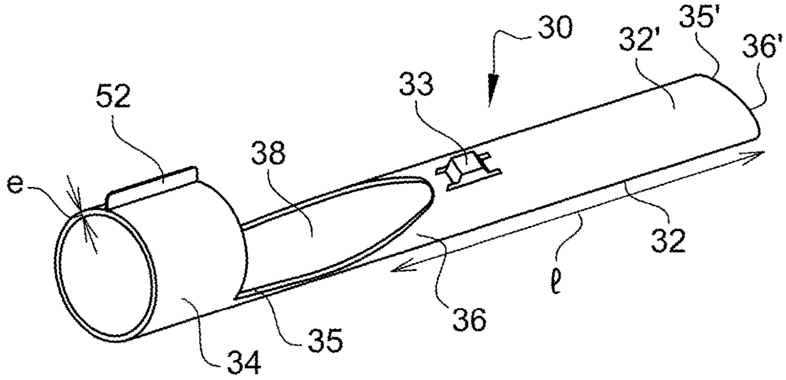
FIG. 4 is a schematic perspective view of a retroperfusion cannula of the arterial cannula of FIG. 2.
Figure 5:
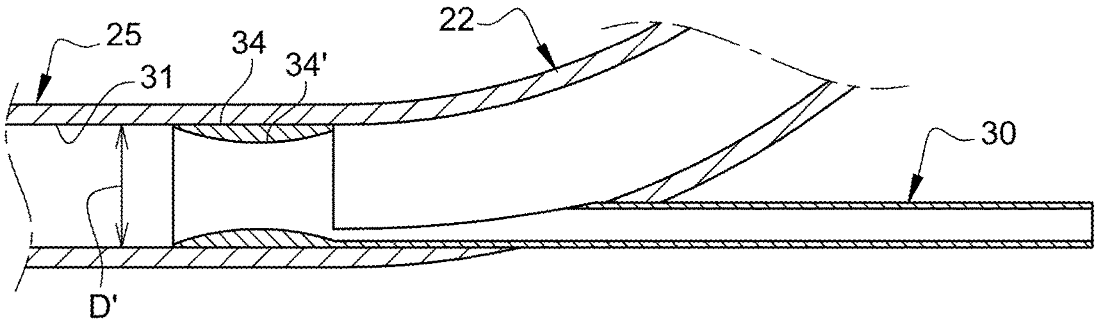
FIG. 5 is a detail view of FIG. 3, illustrating the alignment between the retroperfusion cannula and the main arterial cannula when the retroperfusion cannula is in the deployed position.

Furthermore, as shown in FIG. 4, ring 34 may include a rib 52 configured to cooperate with a groove 50 (FIG. 6) disposed longitudinally in the inner wall 31 of the main arterial cannula 22. The groove 50 may have a length corresponding to the translation length of the retroperfusion cannula 30. Thus, the groove 50 allows limiting and containing the translation of the retro cannula. It allows preventing the retroperfusion cannula 30 from escaping from the first end 24 of the main arterial cannula 22 upon switching from the retracted position into the deployed position, so that the proximal end 36 of the tube 32 stops exactly in the thickness of the wall of the elbow 27 of the main arterial cannula 22 in the deployed position. Furthermore, it allows limiting the translation of the retroperfusion cannula 30 upon switching from the deployed position into the retracted position, such that the distal end 36' of the tube 32 stops exactly within the thickness of the wall of the elbow 27 of the main arterial cannula 22 in the retracted position.

Figure 11:
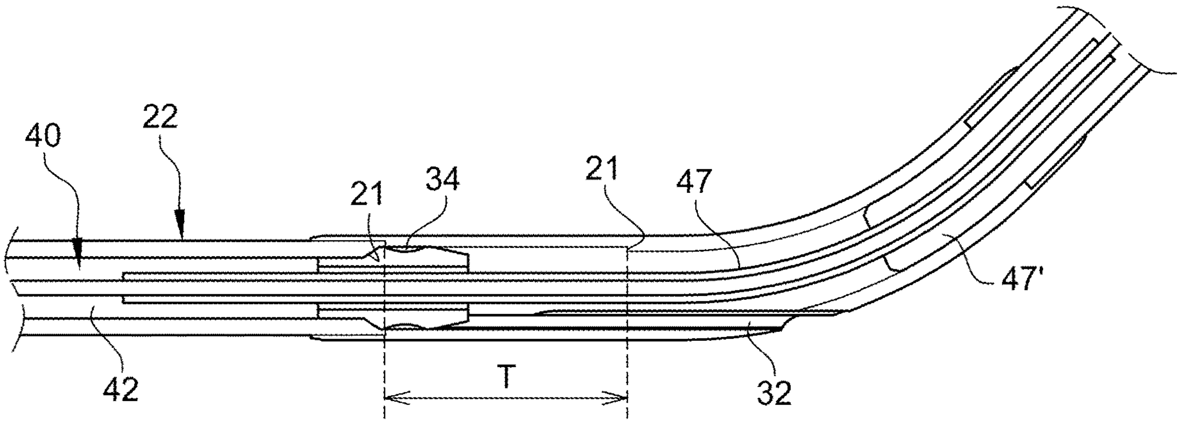
FIG. 11 is another schematic longitudinal sectional view of the arterial cannula, illustrating an embodiment in which the main arterial cannula has a difference in inner diameter of FIG. 10.
Figure 13:
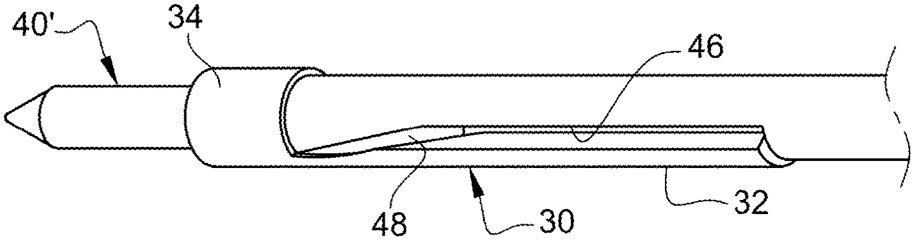
FIG. 13 is a schematic view of the introducer stylet of FIG. 9 inserted into a retroperfusion cannula of an arterial cannula according to the present disclosure.

In one embodiment represented in FIG. 13, the ring 34 does not includes any rib 52 and the inner wall 31 of the main cannula does not have any groove 50. In this embodiment, the main arterial cannula has, outside the translation portion T of the ring 34, an inner diameter smaller than the diameter D of the ring 34 (FIG. 11). Thus, the translation portion T having an inner diameter larger than the inner diameter of the rest of the main arterial cannula, the inner diameter of the translation portion T being very slightly larger than the diameter D of the ring. The translation of the ring is limited upon deployment and/or removal of the retroperfusion cannula by the smaller inner diameter of the main arterial cannula outside the translation portion T of the ring. The difference in diameter forms a stop 21 (FIG. 11) at each end of the translation portion T.

As shown in FIG. 3, the main arterial cannula may have an inner protrusion 51. As will be seen later on, the inner protrusion 51 is configured to limit the translation of an introducer stylet 40 intended to be inserted into the arterial cannula 20.

FIGS. 7 to 11 illustrate a first embodiment of an introducer stylet 40 according to the present disclosure. The introducer stylet is configured to be inserted into an arterial cannula 20 as previously described, before introduction thereof into an artery, in order to enable both the insertion of the main arterial cannula 22 into the artery and the deployment of the retroperfusion cannula 30 out of the main arterial cannula 22. It may have a proximal end 42 in the form of a point, intended to pass through the blood outlet orifice 26 of the main arterial cannula 22, when the introducer stylet 40 is inserted into the arterial cannula, in order to facilitate the introduction of the main arterial cannula 22 into the artery. It may further have a distal end 42' in the form of a clamp, configured to clasp the second end 28 of the arterial cannula.

Figure 7:
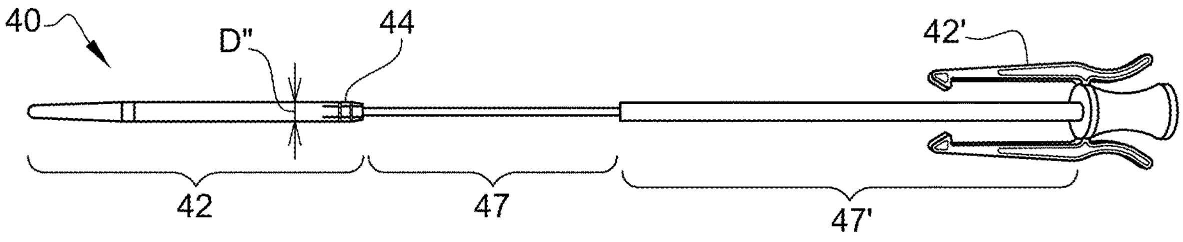
FIG. 7 is a schematic perspective view of an introducer stylet according to a first embodiment.

As shown in FIG. 7, the introducer stylet 40 may advantageously have a first intermediate portion 47, proximal to the proximal end 42, and a second intermediate portion 47', proximal to the distal end 42' in the form of a clamp. The first intermediate portion 47 may have a length slightly larger than that of the retroperfusion cannula. It may have a diameter smaller than the diameter of the main arterial cannula. Thus, the first intermediate portion 47 does not spatially interfere with the retroperfusion cannula when the latter is in the retracted position in the main arterial cannula. On the other hand, the second intermediate portion 47' may have a diameter substantially identical to that of the main arterial cannula in order to have a minimum clearance upon introduction thereof into the arterial cannula. Furthermore, this allows conferring some rigidity on the introducer stylet and enabling an axial and centered progression upon insertion of the introducer stylet into the arterial cannula. However, in order to be non-obstructive, the second intermediate portion 47' may have longitudinal grooves (not represented) enabling blood to circulate.

Figure 6:
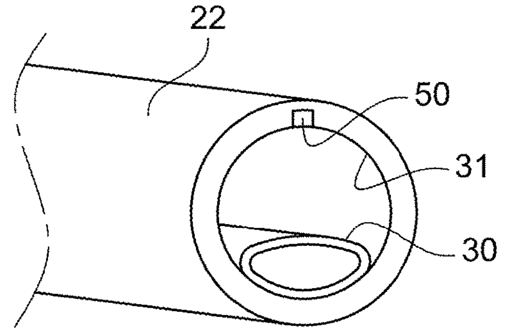
FIG. 6 is a schematic cross-sectional view of the arterial cannula comprising a retroperfusion cannula.

The proximal end 42 of the introducer stylet 40 may have an increasing diameter, up to a maximum diameter D" identical to the inner diameter D' of the main arterial cannula 22, which allows obstructing the main arterial cannula 22. Thus, no blood flow circulates as long as the introducer stylet is disposed in the main arterial cannula. This increasing diameter enables the introducer stylet 40 to be inserted into the first end 24 of the main arterial cannula 20 in which the retroperfusion cannula 30 is disposed in the retracted position. Indeed, the retroperfusion cannula 30 in the retracted position reduces the free inner space of the main arterial cannula (as shown in FIG. 6).

Figure 10:
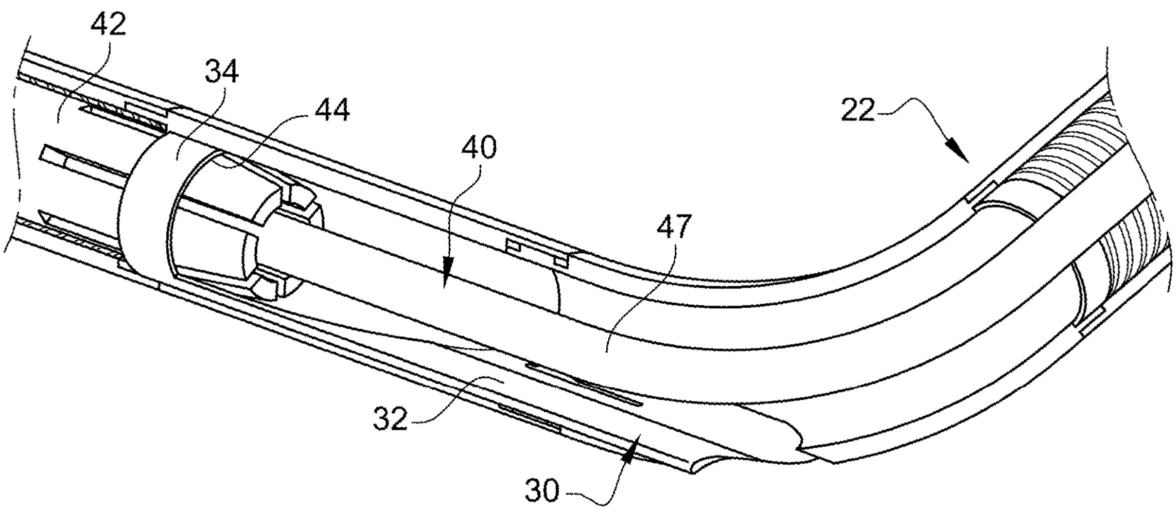
FIG. 10 is a schematic longitudinal sectional view of an arterial cannula portion provided with an introducer stylet according to FIG. 7.

Furthermore, the proximal end 42 of the introducer stylet 40 may be configured to cooperate with the ring 34 of the retroperfusion cannula. To this end, the proximal end 42 may include a groove 44 in which the ring 34 is intended to fit (FIG. 10). The groove 44 allows holding the retroperfusion cannula 30 in the retracted position in the main arterial cannula 22 upon insertion of the main arterial cannula 22 into an artery, and to drive the retroperfusion cannula 30 in its deployed position upon removal of introducer stylet 40 from arterial cannula 20.

The proximal end 42 of the introducer stylet 40 may be configured to abut against the inner protrusion 51 (FIG. 3) of the main arterial cannula, at the maximum diameter D". Thus, the translation of the introducer stylet 40 in the main arterial cannula is limited so that the ring 34 of the retroperfusion cannula fits into the groove 44 of the introducer stylet.

Figure 8:
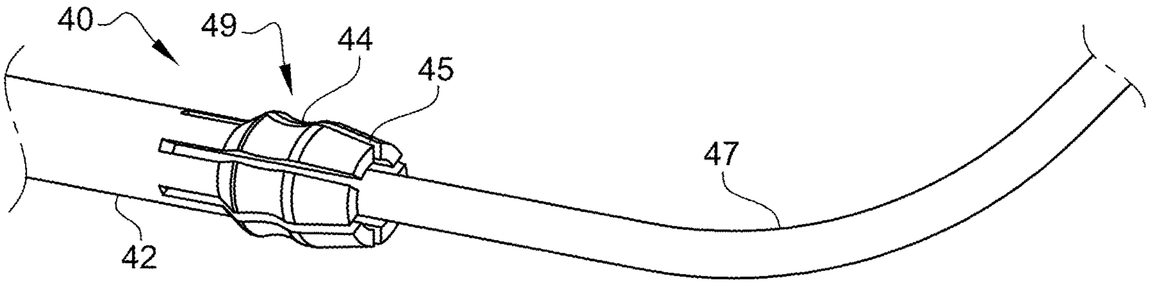
FIG. 8 is a schematic perspective view of a detail of the introducer stylet of FIG. 7.

FIG. 8 shows that the insertion stylet 40 may have incisions 45 at and around the groove 44. These incisions allow forming a deformable retentive system 49. Thus, when the retroperfusion cannula completes its translation in the main arterial cannula upon deployment thereof, the diameter of the stylet at the deformable retentive system retracts slightly enabling it to slip out of the ring to completely free itself from the arterial cannula.

The introducer stylet 40 may be deformable, in order to be able to confer any shape on the main arterial cannula 22. Indeed, the flexible portions of the main arterial cannula 22 are able to be deformed by the introducer stylet 40, so as to impart thereon, for example, a Z-like shape comprising a first free branch corresponding at the first end 24 intended to be introduced into an artery, a central branch and a second free branch intended to cooperate with the oxygenator (not represented).

Figure 9:
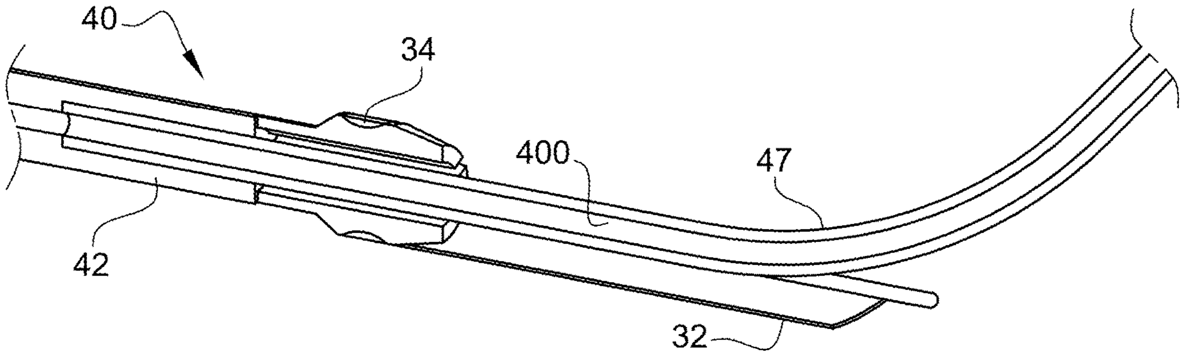
FIG. 9 is a schematic sectional view of the introducer stylet of FIG. 8, inserted into the ring of the retroperfusion cannula according to the present disclosure.

As shown in FIG. 9, the introducer stylet 40 may be axially perforated at its center into a hollow cylinder 400.

Figure 12:
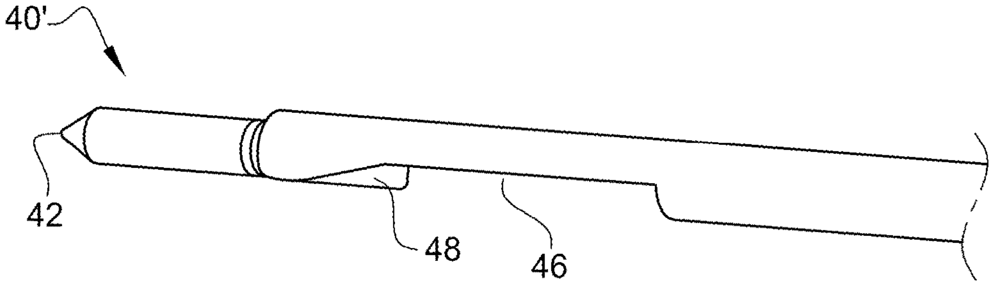
FIG. 12 is a partial schematic view of an introducer stylet according to a second embodiment.

FIGS. 12 and 13 illustrate a second embodiment of an introducer stylet 40' according to the present disclosure.

The introducer stylet 40' may have a recess 46 complementary to the tube 32 of the retroperfusion cannula 30 (FIG. 10), enabling the introducer stylet 40' to be introduced into the first end 24 of the main arterial cannula 20 in which the retroperfusion cannula 30 is disposed in the retracted position. This recess 46 may include a lug 48 configured to cooperate with the tube 32 of the retroperfusion cannula 30 in order to enable the deployment thereof out of the main arterial cannula 22.

The introducer stylet 40 according to the first embodiment is symmetrical with respect to its longitudinal axis and is therefore configured to be introduced into the arterial cannula 20 in any position irrespective of the rotation of the stylet on its axis.

On the other hand, the introducer stylet 40' according to the second embodiment is configured to be introduced into the arterial cannula in an accurate position, so that the recess 46 cooperates with the tube 32 of the retroperfusion cannula 30.

These stylets 40, 40' enable a bidirectional translation of the retroperfusion cannula.

Figure 14:
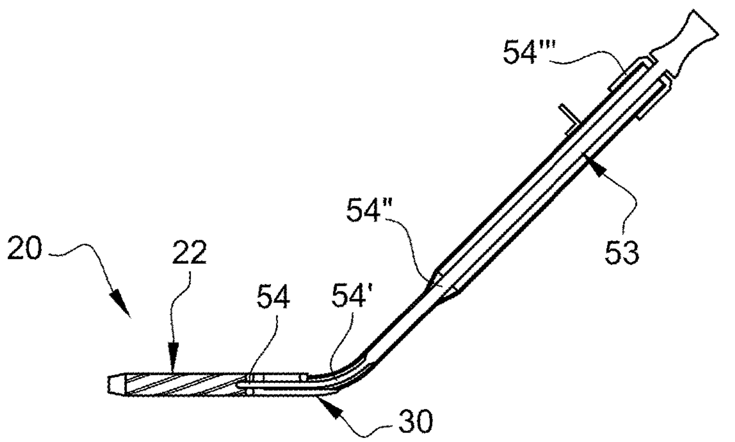
FIG. 14 is a partial schematic view of the arterial cannula according to the present disclosure, provided with a removal stylet inserted into the main cannula.
Figure 15:
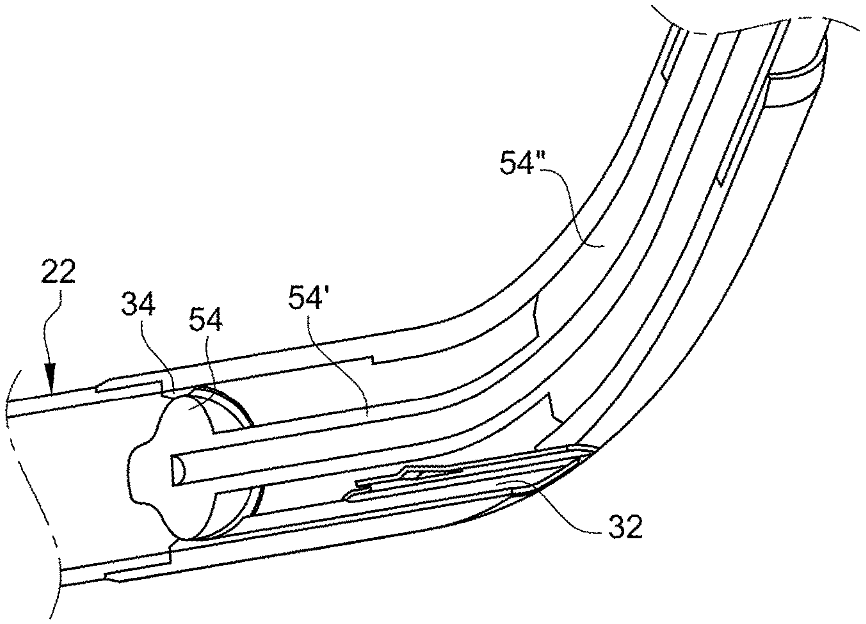
FIG. 15 is a schematic longitudinal sectional view of a portion of the arterial cannula of FIG. 14, detailing the removal stylet.
Figure 16:
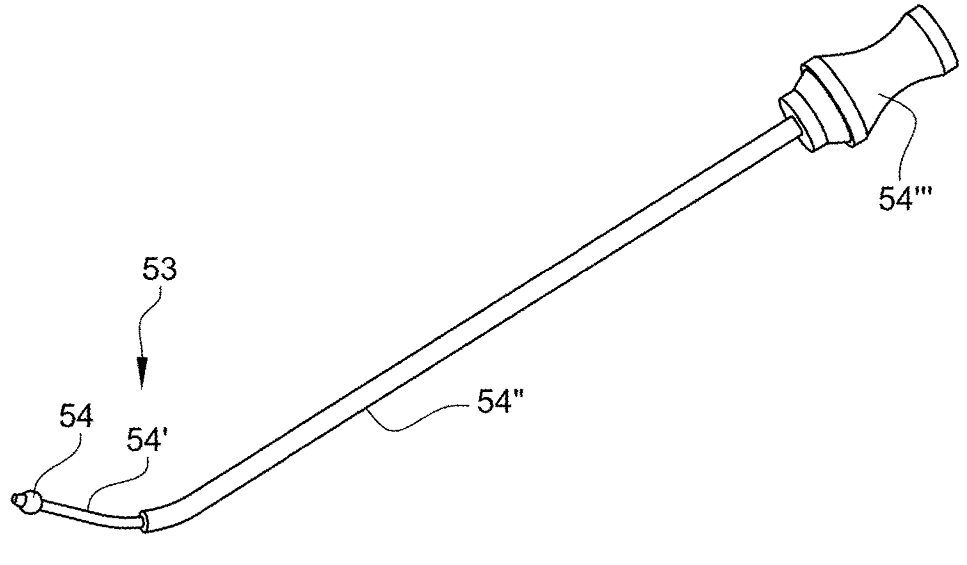
FIG. 16 is a schematic perspective view of the removal stylet of FIGS. 14 and 15.

FIGS. 14-16 illustrate a removal stylet 53 configured to allow retracting the retroperfusion cannula 30 in the main arterial cannula 22, in order to allow retracting the main arterial cannula 22 out of an artery.

The removal stylet 53 is configured to be inserted into an arterial cannula 20 as previously described, when the retroperfusion cannula 30 is in the deployed position, in order to allow retracting the retroperfusion cannula 30 in the main arterial cannula 22. It may have a bulge 54 configured to cooperate with the ring 34 of the retroperfusion cannula 30 in order to drive it in translation in the main arterial cannula 22, when the removal stylet 53 is inserted into the main arterial cannula 22. The bulge 54 may be disposed at a so-called proximal end of the removal stylet 53. The proximal end of the removal stylet 53 is an end intended to be disposed proximate to the blood outlet orifice 26 of the main arterial cannula 22, when the removal stylet 53 is inserted into the arterial cannula 20. The bulge 54 may be intended to fit into the ring 34. It could obstruct the ring 34. The bulge 54 may be spherical. The removal stylet 53 may also have a first intermediate portion 54', preferably cylindrical, whose diameter enables the removal of the retroperfusion cannula without spatial interference therewith upon retraction thereof in the main arterial cannula. This first intermediate portion 54' may have a length identical to that of the retroperfusion cannula. The removal stylet may also have a second intermediate portion 54", preferably cylindrical, whose diameter is equal to that of the main arterial cannula in order to obstruct it to prevent the rise of blood in the main arterial cannula. Moreover, the removal stylet may have a distal end 54" in the form of a cap, configured to cooperate with the second end 28 of the arterial cannula.

The second intermediate portion 54" of the removal stylet 53 may have a diameter identical to the inner diameter D' of the main arterial cannula 22, which allows obstructing the main arterial cannula 22. Thus, no blood flow circulates in the arterial cannula when the removal stylet is disposed in the main arterial cannula.

The bulge 54 is configured to cooperate with the ring 34 which may have a convex inner wall 34' (FIG. 5) in order to drive the retroperfusion cannula 30 in translation in the main arterial cannula 22, upon insertion thereof into the arterial cannula 20.

Furthermore, the convex internal wall 34' of the ring 34 allows laminating the blood flow and thus avoiding hemolysis and turbulent blood flows.

As shown in FIG. 14, the removal stylet 53 allows obstructing the main arterial cannula 22 when inserted into the main arterial cannula.

The invention claimed is:

1. An arterial cannula for ECMO comprising:

a main arterial cannula including an inner wall and having a first end with a blood outlet orifice, the first end being intended to be inserted into an artery in order to inject blood in a retrograde manner into the artery, and a retroperfusion cannula configured to be movable in translation between a retracted position in the first end of the main arterial cannula and a position at least partially deployed out of the first end of the main arterial cannula, the retroperfusion cannula being opposite to the blood outlet orifice of the main arterial cannula, wherein the retroperfusion cannula comprises a tube with a diameter smaller than a diameter of the main arterial cannula, and a ring with a diameter substantially identical to the diameter of the main arterial cannula, the ring being disposed at a proximal end of the retroperfusion cannula with respect to the blood outlet orifice of the main arterial cannula.

2. The arterial cannula according to claim 1, having an L-shape, the arterial cannula comprising a first branch corresponding to the first end intended to be introduced into the artery, and a second branch intended to cooperate with an oxygenator, the first branch and the second branch being connected by an elbow.

3. The arterial cannula according to claim 1, wherein the retroperfusion cannula is configured to slip in translation in contact with the inner wall of the main arterial cannula, until the ring comes into contact with a stop of the inner wall.

4. The arterial cannula according to claim 1, wherein a cutout is present between the tube and the ring.

5. The arterial cannula according to claim 1, wherein the tube has an elliptical profile.

6. The arterial cannula according to claim 1, wherein the ring has a convex internal wall.

7. The arterial cannula according to claim 1, wherein the inner wall of the main arterial cannula comprises a longitudinal groove, and the ring of the retroperfusion cannula comprises a rib, the longitudinal groove cooperating with the rib.

8. The arterial cannula according to claim 1, wherein the main arterial cannula comprises a translation portion of the ring, the translation portion of the ring having an inner diameter larger than an inner diameter of a non-translation portion of the main arterial cannula.

9. The arterial cannula according to claim 2, wherein the tube has a beveled distal end, opposite to the ring, to be adapted to a curvature of the elbow of the main arterial cannula when the retroperfusion cannula is in the retracted position, the tube including an opening directed towards the second branch of the main arterial cannula.

10. A kit comprising an arterial cannula according to claim 1, further including an introducer stylet configured to be inserted into the arterial cannula to enable both an insertion of the main arterial cannula into an artery and a deployment of the retroperfusion cannula out of the main arterial cannula, the introducer stylet being configured to obstruct the main arterial cannula, and a removal stylet configured to be inserted into the arterial cannula to allow retracting the retroperfusion cannula in the main arterial cannula, and to allow removing the main arterial cannula out of the artery, the removal stylet being configured to obstruct the main arterial cannula.

* * * * *